US008244346B2

(12) United States Patent
Foster et al.

(10) Patent No.: US 8,244,346 B2
(45) Date of Patent: Aug. 14, 2012

(54) LEAD WITH MRI COMPATIBLE DESIGN FEATURES

(75) Inventors: Arthur J. Foster, Centerville, MN (US); Jean M. Bobgan, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 484 days.

(21) Appl. No.: 12/364,181

(22) Filed: Feb. 2, 2009

(65) Prior Publication Data
US 2009/0198314 A1    Aug. 6, 2009

Related U.S. Application Data

(60) Provisional application No. 61/026,661, filed on Feb. 6, 2008.

(51) Int. Cl.
*A61N 1/05* (2006.01)

(52) U.S. Cl. ........... 607/2; 600/411; 607/116; 607/122; 128/901

(58) Field of Classification Search .................. 600/411
See application file for complete search history.

(56) References Cited

U.S. PATENT DOCUMENTS

| | | | |
|---|---|---|---|
| 3,614,692 A | 10/1971 | Rozelle et al. | |
| 4,131,759 A | 12/1978 | Felkel | |
| 4,135,518 A | 1/1979 | Dutcher | |
| 4,404,125 A | 9/1983 | Abolins et al. | |
| 4,484,586 A | 11/1984 | McMickle et al. | |
| 4,493,329 A | 1/1985 | Crawford et al. | |
| 4,643,202 A | 2/1987 | Roche | |
| 4,869,970 A | 9/1989 | Gulla et al. | |
| 5,056,516 A | 10/1991 | Spehr | |
| 5,217,010 A | 6/1993 | Tsitlik et al. | |
| 5,222,506 A * | 6/1993 | Patrick et al. | 607/126 |
| 5,231,996 A | 8/1993 | Bardy et al. | |
| 5,243,911 A | 9/1993 | Dow et al. | |
| 5,246,014 A * | 9/1993 | Williams et al. | 607/122 |
| 5,330,522 A | 7/1994 | Kreyenhagen | |
| 5,378,234 A | 1/1995 | Hammerslag et al. | |
| 5,387,199 A | 2/1995 | Siman et al. | |
| 5,425,755 A | 6/1995 | Doan | |
| 5,456,707 A | 10/1995 | Giele | |

(Continued)

FOREIGN PATENT DOCUMENTS

| | | |
|---|---|---|
| EP | 0897997 B1 | 2/1999 |
| JP | 2004141679 A | 5/2004 |
| JP | 2005501673 A | 1/2005 |

(Continued)

OTHER PUBLICATIONS

International Search Report and Written Opinion issued in PCT/US2010/024062, mailed Sep. 27, 2010.
Invitation to Pay Additional Fees and Partial Search Report, issued in PCT/US20101024062, mailed May 7, 2010.

(Continued)

*Primary Examiner* — Kennedy Schaetzle
(74) *Attorney, Agent, or Firm* — Faegre Baker Daniels LLP

(57) ABSTRACT

Implantable medical leads with magnetic shielding and methods of shielding implantable leads from magnetic fields during medical procedures such as magnetic resonance imaging (MRI) are disclosed. An exemplary implantable medical lead includes a helically coiled inner electrode conductor wire, a helically coiled outer electrode conductor wire disposed radially about the inner electrode conductor wire, and at least one layer of insulation that electrically isolates the inner and outer electrode conductor wires. The inner electrode conductor wire can have a hollowed, multifilar configuration including six or more co-radially wound wire filars. The outer electrode conductor wire is electrically isolated from the inner electrode conductor wire, and may have either a single or double filar configuration.

20 Claims, 3 Drawing Sheets

U.S. PATENT DOCUMENTS

| | | | |
|---|---|---|---|
| 5,483,022 A | | 1/1996 | Mar |
| 5,522,872 A | * | 6/1996 | Hoff ............................ 607/119 |
| 5,522,875 A | | 6/1996 | Gates et al. |
| 5,554,139 A | | 9/1996 | Okajima |
| 5,574,249 A | | 11/1996 | Lindsay |
| 5,584,873 A | | 12/1996 | Shoberg et al. |
| 5,599,576 A | | 2/1997 | Opolski |
| 5,618,208 A | | 4/1997 | Crouse et al. |
| 5,760,341 A | | 6/1998 | Laske et al. |
| 5,800,496 A | | 9/1998 | Swoyer et al. |
| 5,810,887 A | | 9/1998 | Accorti, Jr. et al. |
| 5,935,159 A | | 8/1999 | Cross, Jr. et al. |
| 5,957,970 A | | 9/1999 | Shoberg et al. |
| 5,968,087 A | | 10/1999 | Hess et al. |
| 6,057,031 A | | 5/2000 | Breme et al. |
| 6,078,840 A | | 6/2000 | Stokes |
| 6,106,522 A | | 8/2000 | Fleischman et al. |
| 6,143,013 A | | 11/2000 | Samson et al. |
| 6,178,355 B1 | | 1/2001 | Williams et al. |
| 6,208,881 B1 | | 3/2001 | Champeau |
| 6,249,708 B1 | | 6/2001 | Nelson et al. |
| 6,256,541 B1 | | 7/2001 | Heil et al. |
| 6,289,250 B1 | | 9/2001 | Tsuboi et al. |
| 6,295,476 B1 | | 9/2001 | Schaenzer |
| 6,400,992 B1 | | 6/2002 | Borgersen et al. |
| 6,434,430 B2 | | 8/2002 | Borgersen et al. |
| 6,456,888 B1 | * | 9/2002 | Skinner et al. ................. 607/116 |
| 6,493,591 B1 | | 12/2002 | Stokes |
| 6,501,991 B1 | | 12/2002 | Honeck et al. |
| 6,501,994 B1 | | 12/2002 | Janke et al. |
| 6,510,345 B1 | | 1/2003 | Van entem |
| 6,516,230 B2 | | 2/2003 | Williams et al. |
| 6,526,321 B1 | | 2/2003 | Spehr |
| 6,564,107 B1 | | 5/2003 | Bodner et al. |
| 6,671,554 B2 | | 12/2003 | Gibson et al. |
| 6,721,604 B1 | | 4/2004 | Robinson et al. |
| 6,813,521 B2 | | 11/2004 | Bischoff et al. |
| 6,850,803 B1 | | 2/2005 | Jimenez et al. |
| 6,854,994 B2 | | 2/2005 | Stein et al. |
| 6,925,334 B1 | | 8/2005 | Salys |
| 6,949,929 B2 | | 9/2005 | Gray et al. |
| 6,978,185 B2 | | 12/2005 | Osypka |
| 6,993,373 B2 | | 1/2006 | Vrijheid et al. |
| 6,999,821 B2 | | 2/2006 | Jenney et al. |
| 7,013,180 B2 | | 3/2006 | Villaseca et al. |
| 7,013,182 B1 | | 3/2006 | Krishnan |
| 7,123,013 B2 | | 10/2006 | Gray |
| 7,138,582 B2 | | 11/2006 | Lessar et al. |
| 7,174,219 B2 | | 2/2007 | Wahlstrand et al. |
| 7,174,220 B1 | | 2/2007 | Chitre et al. |
| 7,205,768 B2 | | 4/2007 | Schulz |
| 7,363,090 B2 | | 4/2008 | Halperin et al. |
| 7,388,378 B2 | | 6/2008 | Gray et al. |
| 7,389,148 B1 | | 6/2008 | Morgan |
| 7,610,101 B2 | | 10/2009 | Wedan et al. |
| 2002/0072769 A1 | | 6/2002 | Silvian et al. |
| 2002/0111664 A1 | | 8/2002 | Bartig et al. |
| 2002/0128689 A1 | | 9/2002 | Connelly et al. |
| 2002/0144720 A1 | | 10/2002 | Zahorik et al. |
| 2003/0083723 A1 | | 5/2003 | Wilkinson et al. |
| 2003/0083726 A1 | | 5/2003 | Zeijlemaker et al. |
| 2003/0092303 A1 | | 5/2003 | Osypka |
| 2003/0093138 A1 | * | 5/2003 | Osypka et al. ................. 607/122 |
| 2003/0140931 A1 | | 7/2003 | Zeijlemaker et al. |
| 2003/0144705 A1 | | 7/2003 | Funke |
| 2003/0144716 A1 | | 7/2003 | Reinke et al. |
| 2003/0144718 A1 | | 7/2003 | Zeijlemaker |
| 2003/0144719 A1 | | 7/2003 | Zeijlemaker |
| 2003/0144720 A1 | | 7/2003 | Villaseca et al. |
| 2003/0144721 A1 | | 7/2003 | Villaseca et al. |
| 2003/0204217 A1 | | 10/2003 | Greatbatch |
| 2004/0064173 A1 | * | 4/2004 | Hine et al. .................... 607/122 |
| 2004/0088033 A1 | * | 5/2004 | Smits et al. ................... 607/122 |
| 2004/0122490 A1 | | 6/2004 | Reinke et al. |
| 2004/0162600 A1 | | 8/2004 | Williams |
| 2004/0193140 A1 | | 9/2004 | Griffin et al. |
| 2004/0267107 A1 | * | 12/2004 | Lessar et al. .................. 600/395 |
| 2005/0070972 A1 | | 3/2005 | Wahlstrand et al. |
| 2005/0090886 A1 | | 4/2005 | MacDonald et al. |
| 2005/0113676 A1 | | 5/2005 | Weiner et al. |
| 2005/0113873 A1 | | 5/2005 | Weiner et al. |
| 2005/0113876 A1 | | 5/2005 | Weiner et al. |
| 2005/0222642 A1 | | 10/2005 | Przybyszewski et al. |
| 2005/0222656 A1 | | 10/2005 | Wahlstrand et al. |
| 2005/0222657 A1 | | 10/2005 | Wahlstrand et al. |
| 2005/0222658 A1 | | 10/2005 | Hoegh et al. |
| 2005/0222659 A1 | | 10/2005 | Olsen et al. |
| 2005/0246007 A1 | | 11/2005 | Sommer et al. |
| 2005/0283167 A1 | | 12/2005 | Gray |
| 2006/0009819 A1 | | 1/2006 | Przybyszewski |
| 2006/0030774 A1 | | 2/2006 | Gray et al. |
| 2006/0041294 A1 | | 2/2006 | Gray |
| 2006/0089691 A1 | | 4/2006 | Kaplan et al. |
| 2006/0089695 A1 | | 4/2006 | Bolea et al. |
| 2006/0089696 A1 | | 4/2006 | Olsen et al. |
| 2006/0106442 A1 | | 5/2006 | Richardson et al. |
| 2006/0167536 A1 | | 7/2006 | Nygren et al. |
| 2006/0200218 A1 | | 9/2006 | Wahlstrand |
| 2006/0229693 A1 | | 10/2006 | Bauer et al. |
| 2006/0247747 A1 | | 11/2006 | Olsen et al. |
| 2006/0247748 A1 | | 11/2006 | Wahlstrand et al. |
| 2006/0271138 A1 | | 11/2006 | MacDonald |
| 2006/0293737 A1 | * | 12/2006 | Krishnan ....................... 607/122 |
| 2007/0106332 A1 | | 5/2007 | Denker et al. |
| 2007/0156205 A1 | | 7/2007 | Larson et al. |
| 2007/0179577 A1 | | 8/2007 | Marshall et al. |
| 2007/0179582 A1 | | 8/2007 | Marshall et al. |
| 2007/0191914 A1 | | 8/2007 | Stessman |
| 2007/0208383 A1 | | 9/2007 | Williams |
| 2008/0033497 A1 | | 2/2008 | Bulkes et al. |
| 2008/0049376 A1 | | 2/2008 | Stevenson et al. |
| 2008/0058902 A1 | | 3/2008 | Gray et al. |
| 2008/0125754 A1 | | 5/2008 | Beer et al. |
| 2008/0129435 A1 | | 6/2008 | Gray |
| 2008/0132986 A1 | | 6/2008 | Gray et al. |
| 2008/0243218 A1 | | 10/2008 | Bottomley et al. |
| 2008/0262584 A1 | * | 10/2008 | Bottomley et al. ............ 607/119 |
| 2009/0099440 A1 | | 4/2009 | Viohl |
| 2009/0099555 A1 | | 4/2009 | Viohl et al. |
| 2009/0118610 A1 | | 5/2009 | Karmarkar et al. |
| 2009/0149920 A1 | * | 6/2009 | Li et al. .......................... 607/63 |
| 2009/0149933 A1 | | 6/2009 | Ameri |
| 2009/0281608 A1 | | 11/2009 | Foster |
| 2010/0010602 A1 | | 1/2010 | Wedan et al. |
| 2010/0234929 A1 | | 9/2010 | Scheuermann |
| 2010/0331936 A1 | | 12/2010 | Perrey et al. |
| 2011/0087299 A1 | | 4/2011 | Ameri |
| 2011/0093054 A1 | | 4/2011 | Ameri |
| 2011/0238146 A1 | | 9/2011 | Wedan et al. |

FOREIGN PATENT DOCUMENTS

| | | |
|---|---|---|
| JP | 2005515852 A | 6/2005 |
| JP | 2005515854 A | 6/2005 |
| WO | 03/063946 | 8/2003 |
| WO | WO 03/089045 | 10/2003 |
| WO | 2005/030322 | 4/2005 |
| WO | 2006/105066 | 10/2006 |
| WO | WO 2007/047966 | 4/2007 |
| WO | WO 2007/089986 | 8/2007 |
| WO | WO 2007/118194 | 10/2007 |
| WO | 2006/093685 | 9/2009 |

OTHER PUBLICATIONS

Robert W. Gray, et al., Simple design changes to wires to substantially reduce MRI-induced heating at 1.5T: implications for implanted leads, Magnetic Resonance Imaging, vol. 23, Oct. 8, 2005, pp. 887-891.

International Search Report and Written Opinion issued in PCT/US2010/033686 on Aug. 10, 2010, 12 pages.

International Search Report and Written Opinion issued in PCT/US2008/085518 on Oct. 29, 2009, 15 pages.

Invitation to Pay Additional Fees and Partial Search Report, dated Aug. 17, 2009, issued in PCT/US2008/085533, 6 pages.

* cited by examiner

LEAD WITH MRI COMPATIBLE DESIGN FEATURES

CROSS REFERENCE TO RELATED APPLICATION

This application claims priority under 35 U.S.C. §119 to U.S. Provisional Application No. 61/026,661, filed on Feb. 6, 2008, entitled "Lead With MRI Compatible Design Features," which is incorporated herein by reference in its entirety for all purposes.

TECHNICAL FIELD

The present invention relates to medical devices and the simultaneous delivery of diagnostic and therapeutic treatments. More specifically, the present invention relates to implantable medical leads with magnetic shielding and methods of shielding such leads from magnetic fields during medical procedures such as magnetic resonance imaging (MRI).

BACKGROUND

Magnetic resonance imaging (MRI) is a non-invasive imaging method that utilizes nuclear magnetic resonance techniques to render images within a patient's body. Typically, MRI systems employ the use of a magnetic coil having a magnetic field strength of between about 0.2 to 3 Teslas. During the procedure, the body tissue is briefly exposed to RF pulses of electromagnetic energy in a plane perpendicular to the magnetic field. The resultant electromagnetic energy from these pulses can be used to image the body tissue by measuring the relaxation properties of the excited atomic nuclei in the tissue.

During imaging, the electromagnetic radiation produced by the MRI system may be picked up by implantable device leads used in implantable medical devices such as pacemakers or cardiac defibrillators. This energy may be transferred through the lead to the electrode in contact with the tissue, which may lead to elevated temperatures at the point of contact. The degree of tissue heating is typically related to factors such as the length of the lead, the conductivity or impedance of the lead, and the surface area of the lead electrodes. Exposure to a magnetic field may also induce an undesired voltage on the lead.

SUMMARY

The present invention relates to implantable medical leads with magnetic shielding and methods of shielding implantable leads from magnetic fields during medical procedures such as magnetic resonance imaging (MRI). An illustrative medical device includes a pulse generator and a lead having a helically coiled inner electrode conductor wire, a helically coiled outer electrode conductor wire, and one or more insulation layers. The inner electrode conductor wire has a hollowed, multifilar configuration including six or more co-radially wound wire filars. The outer electrode conductor wire is electrically isolated from the inner electrode conductor wire, and has either a single filar or double filar configuration with a relatively high inductance that is adapted to dissipate electromagnetic energy received by the lead during a magnetic resonance procedure.

Figure 1:
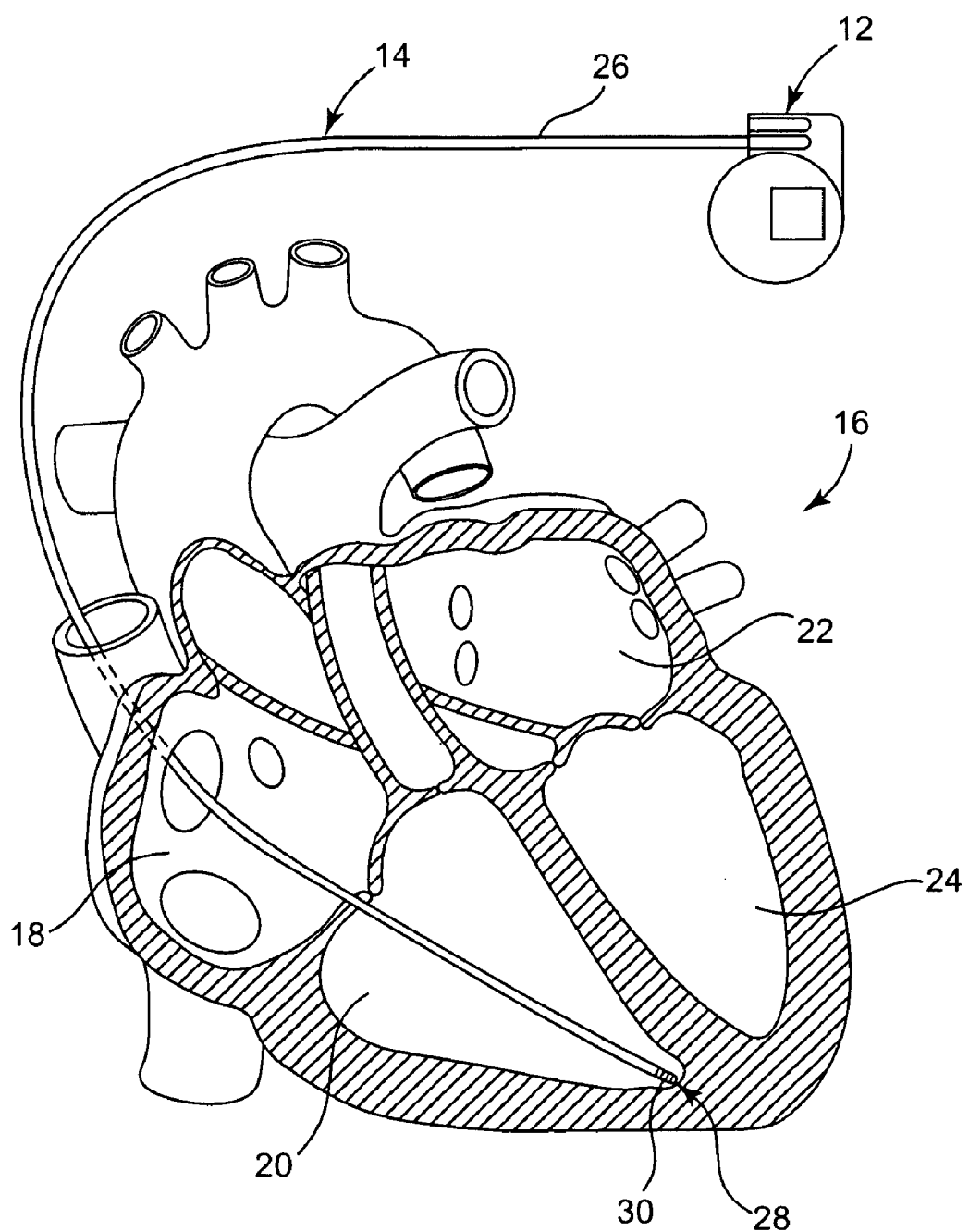
FIG. 1 is a schematic view of an illustrative medical device having a lead implanted within the body of a patient.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view of an illustrative medical device 12 having with a lead implanted within the body of a patient. In the illustrative embodiment depicted, the medical device 12 comprises a pulse generator implanted within the body. The pulse generator 12 is coupled to a lead 14 inserted into the patient's heart 16. The heart 16 includes a right atrium 18, a right ventricle 20, a left atrium 22, and a left ventricle 24. The pulse generator 12 can be implanted subcutaneously within the body, typically at a location such as in the patient's chest or abdomen, although other implantation locations are possible.

A proximal section 26 of the lead 14 can be coupled to or formed integrally with the pulse generator 12. A distal section 28 of the lead 14, in turn, can be implanted at a desired location in or near the heart 16 such as in the right ventricle 20, as shown. In use, one or more electrodes 30 on the distal section 28 of the lead 14 may provide therapy to the patient in the form of an electrical current to the heart 16. In certain embodiments, for example, the electrode(s) 30 may be provided as part of a cardiac lead 14 used to treat bradycardia, tachycardia, or other cardiac arrhythmias.

Although the illustrative embodiment depicts only a single lead 14 inserted into the patient's heart 16, in other embodiments multiple leads can be utilized so as to electrically stimulate other areas of the heart 16. In some embodiments, for example, the distal section of a second lead (not shown) may be implanted in the right atrium 18. In addition, or in lieu, another lead may be implanted in or near the left side of the heart 16 (e.g., in the coronary veins) to stimulate the left side of the heart 16. Other types of leads such as epicardial leads may also be utilized in addition to, or in lieu of, the lead 14 depicted in FIG. 1.

During operation, the lead 14 can be configured to convey electrical signals between the pulse generator 12 and the heart 16. For example, in those embodiments where the pulse generator 12 is a pacemaker, the lead 14 can be utilized to deliver electrical therapeutic stimulus for pacing the heart 16. For example, in the treatment of bradycardia or tachycardia, the pulse generator 12 can be utilized to deliver electrical stimulus in the form of pacing pulses to the heart 16. In other embodiments in which the pulse generator 12 is an implantable cardiac defibrillator, the lead 14 can be utilized to delver electric shocks to the heart 16 in response to an event such as a heart attack or arrhythmia. In some embodiments, the pulse generator 12 includes both pacing and defibrillation capabilities.

When the pulse generator 12 is subjected to a magnetic field from an MRI scanner or other external magnetic source, electromagnetic radiation is produced within the body that can be picked up by the lead 14 and transferred to the lead electrode(s) 30 in contact with the body tissue. This electromagnetic radiation can cause heating at the interface of the lead electrode(s) 30 and body tissue, and can interfere with the therapeutic electrical currents transmitted by the pulse generator 12 through the lead 14.

Figure 2:
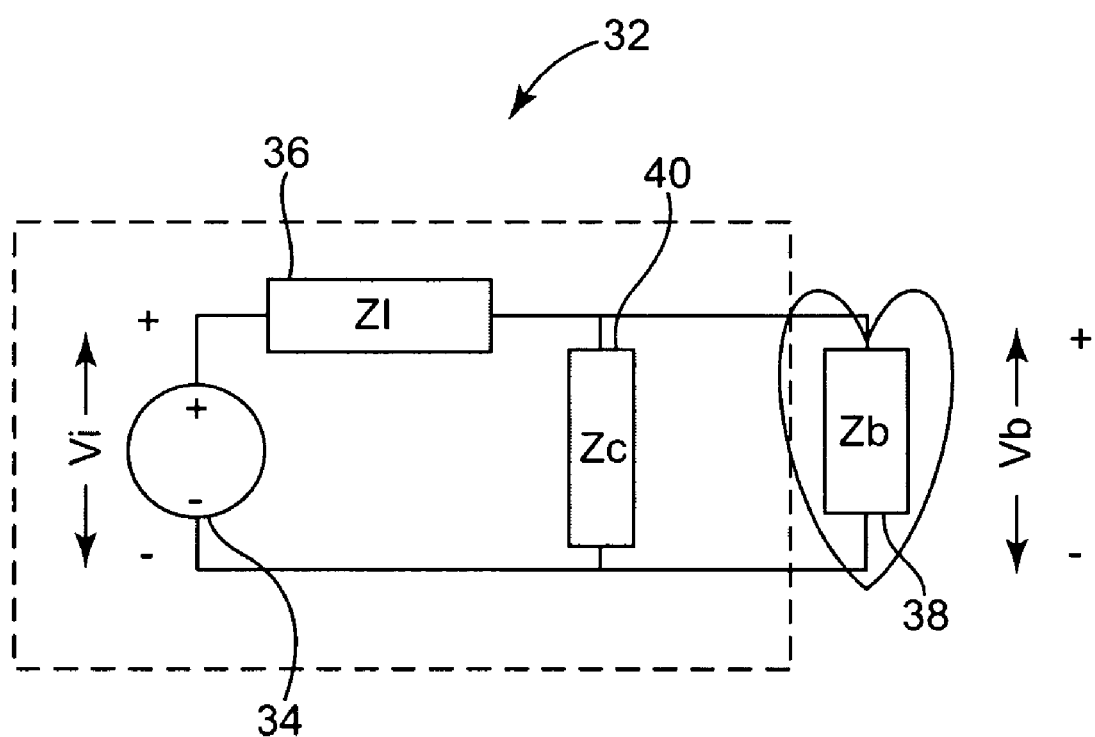
FIG. 2 is a schematic view showing a simplified equivalence circuit for the lead of FIG. 1.

FIG. 2 is a schematic view showing a simplified equivalence circuit 32 for the lead 14 of FIG. 1, representing the RF energy picked up on the lead 14 from RF electromagnetic energy produced by an MRI scanner. As shown in FIG. 2, Vi 34 in the circuit 32 represents an equivalent source of energy picked up by the lead 14 from the MRI scanner. During magnetic resonance imaging, the length of the lead 14 functions similar to an antenna, receiving the RF energy that is transmitted into the body from the MRI scanner. Voltage (Vi) 34 in FIG. 2 may represent, for example, the resultant voltage received by the lead 14 from the RF energy. The RF energy picked up by the lead 14 may result, for example, from the rotating RF magnetic field produced by an MRI scanner, which generates an electric field in the plane perpendicular to the rotating magnetic field vector in conductive tissues. The tangential components of these electric fields along the length of the lead 14 couple to the lead 14. The voltage (Vi) 34 is thus equal to the integration of the tangential electric field (i.e., the line integral of the electric field) along the length of the lead 14.

The ZI parameter 36 in the circuit 32 represents the equivalent impedance exhibited by the lead 14 at the RF frequency of the MRI scanner. The impedance value ZI 36 may represent, for example, the inductance or the equivalent impedance resulting from the parallel inductance and the coil turn by turn capacitance exhibited by the lead 14 at an RF frequency of 64 MHz for a 1.5 Tesla MRI scanner, or at an RF frequency of 128 MHz for a 3 Tesla MRI scanner. The impedance ZI of the lead 14 is a complex quantity having a real part (i.e., resistance) and an imaginary part (i.e., reactance).

Zb 38 in the circuit 32 may represent the impedance of the body tissue at the point of lead contact. Zc 40, in turn, may represent the capacitive coupling of the lead 14 to surrounding body tissue along the length of the lead 14, which may provide a path for the high frequency current (energy) to leak into the surrounding tissue at the RF frequency of the MRI scanner. Minimizing the absorbed energy (represented by source Vi 34) reduces the energy that is transferred to the body tissue at the point of lead contact with the body tissue.

As can be further seen in FIG. 2, the lead 14 has some amount of leakage 40 into the surrounding tissue at the RF frequency of the MRI scanner. As further indicated by 38, there is also an impedance at the point of contact of the lead electrode(s) 30 to the surrounding body tissue within the heart 16. The resulting voltage Vb delivered to the body tissue may be related by the following formula:

$$Vb = Vi\, Zbe/(Zbe+ZI), \text{ where } Zbe=Zb \text{ in parallel with } Zc.$$

The temperature at the tip of the lead 14 where contact is typically made to the surrounding tissue is related in part to the power dissipated at 38 (i.e., at "Zb"), which, in turn, is related to the square of Vb. To minimize temperature rises resulting from the power dissipated at 38, it is thus desirable to minimize Vi (34) and Zc (40) while also maximizing the impedance ZI (36) of the lead 14. In some embodiments, the impedance ZI (36) of the lead 14 can be increased at the RF frequency of the MRI scanner, which aids in reducing the energy dissipated into the surrounding body tissue at the point of contact 38.

In some embodiments, the impedance of the lead 14 can be increased by adding inductance to the lead 14 and/or by a suitable construction technique. For example, the inductance of the lead 14 can be increased by increasing the diameter of the conductor coil(s) and/or by decreasing the pitch of the conductor coil(s) used to supply electrical energy to the electrode(s) 30. Decreasing the coil pitch may result in increasing capacitance between successive turns of the coil (i.e., coil turn by turn capacitance). The parallel combination of inductance (from the helical shape of the coil) and the turn by turn capacitance constitutes a resonance circuit. For a helically coiled lead construction, if the resonance frequency of the lead is above the RF frequency of the MRI, then the helical coil acts as an inductor. For an inductor, increasing the cross section of the coil area and/or reducing the coil pitch increases the inductance and, as a result, increases the impedance of the lead 14.

Similar to an antenna, the energy pickup from a lead is related to its resonance length with respect to the wavelength of the frequency of interest. For example, for a dipole antenna, the antenna is considered tuned, or at resonance, when the antenna length is half the wavelength or an integer multiple of the wavelength. At resonance lengths, the energy pickup of the antenna is maximized. In a similar manner, and in some embodiments, the lead 14 can be detuned so as to prevent resonance within the lead 14, and thus minimize the voltage Vi. For the illustrative embodiment shown in FIG. 1, for example, the lead 14 functions as an antenna having a resonance frequency at length $L=\text{integer} \times \lambda/2$. In some embodiments, the length of the lead 14 and/or the construction parameters of the lead 14 affecting the wavelength can be chosen so as to avoid resonance within the lead 14.

In some embodiments, in addition to detuning the length of the lead 14 with respect to the wavelength of the MRI induced RF energy, shielding can also be added to the lead 14 to further reduce the amount of electromagnetic energy picked up from the lead 14. For example, the energy picked up from the shielding can be coupled to the patient's body along the length of the lead 14, preventing the energy from coupling to the lead tip. The transfer of intercepted energy by the shielding along the length of the shielding/lead can also be inhibited by dissipating the energy as resistive loss, using resistive material for the shielding construction.

Figure 3:
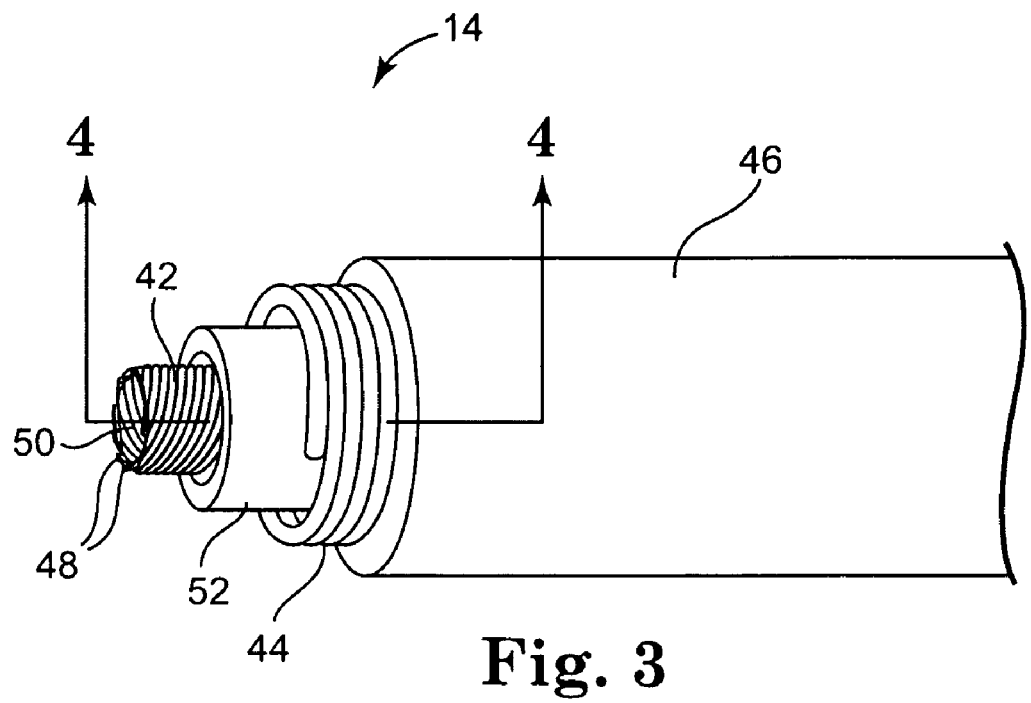
FIG. 3 is a view showing the interior construction of the lead of FIG. 1 in accordance with an exemplary embodiment.

FIG. 3 is a view showing the interior construction of the lead 14 of FIG. 1 in accordance with an exemplary embodiment. In the embodiment of FIG. 3, the lead 14 includes an inner electrode conductor wire 42, an outer electrode conductor wire 44, and an insulation layer 46 disposed radially about the outer electrode conductor wire 44. The inner conductor wire 42 can have any number of different configurations known in the art, including but not limited to, a coiled configuration, a cable configuration, a straight wire configuration, or the like.

In the illustrative embodiment of FIG. 3, the inner conductor wire 42 comprises a helically-shaped multifilar coil conductor wire having a number of filar strands 48 that are tightly wound together to form an inner electrode used to deliver electrical stimulus energy through the lead 14. In one embodiment, for example, the inner conductor wire 42 includes six or more filar strands 48 forming a helically-shaped conductor. In other embodiments, the inner conductor wire 42 can include a greater or lesser number of filar strands 48. In one embodiment, for example, the inner conductor wire 42 may comprise twelve co-radially wound filar strands 48. In some embodiments, each of the filar strands 48 forming the inner conductor wire 42 can comprise a silver-filled MP35N wire having a silver content of about 10% to 28% by cross-sectional area.

In some embodiments, the inner conductor wire 42 has a hollowed configuration, including an interior lumen 50 extending through the wire 42 and adapted to receive a stylet or guidewire that can be used facilitate implantation of the lead 14 within the body. In certain embodiments, the inner conductor wire 42 can be fabricated by co-radially winding a number of wire filars about a mandrel having a diameter that is slightly greater than the diameter of the stylet or guidewire to be inserted into the lumen 50. To improve the torque characteristics of the wire 42, the wire filars 48 can be tightly wound together during fabrication of the wire 42 such that no gaps or spaces exist between the filar strands 48.

As further shown in FIG. 3, and in some embodiments, the outer conductor wire 44 is coaxially disposed about the inner conductor wire 42 and has a helically coiled configuration that extends along all or a portion of the length of the lead 14. In some embodiments, the outer conductor wire 44 has a single-filar construction formed from a single wound wire. In other embodiments, the outer conductor 44 has a multifilar construction formed from multiple, co-radially wound wire filars. In one embodiment, for example, the outer conductor wire 44 has a double-filar construction formed from two co-radially wound wire filars.

The outer conductor wire 44 can be spaced radially apart from the inner conductor wire 44, electrically isolating the outer conductor wire 44 from the inner conductor wire 42. In some embodiments, for example, the outer conductor wire 44 is electrically isolated from the inner conductor wire 42 so that the lead 14 can function as a multipolar lead. In certain embodiments, a second layer of insulation 52 interposed between the inner conductor wire 42 and the outer conductor wire 44 is further used to electrically isolate the conductor wires 42, 44 from each other. In some embodiments, for example, the second layer of insulation 52 may comprise a sheath made from silicon, polyurethane, or other suitable polymeric material.

Figure 4:
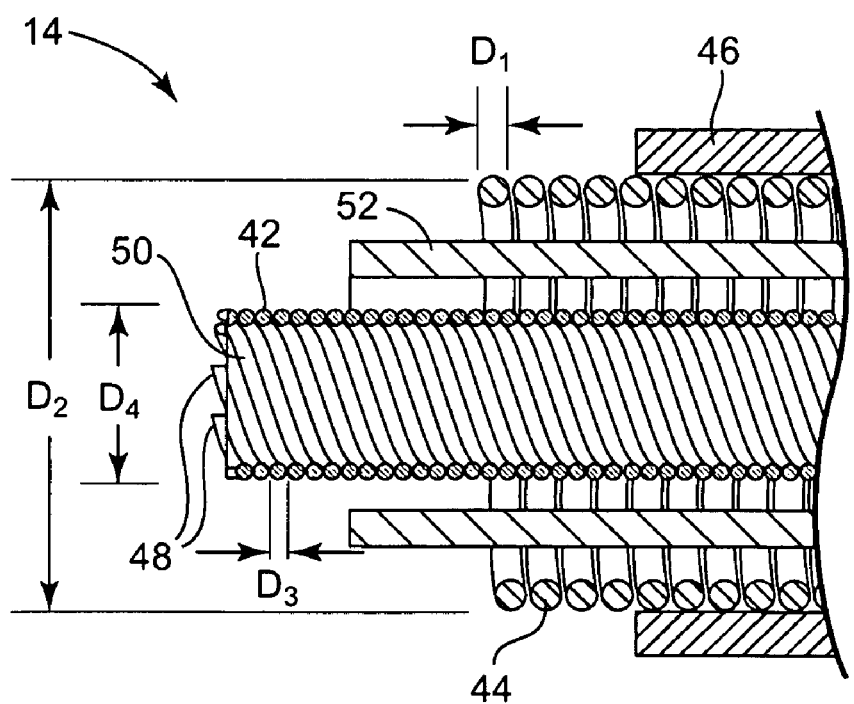
FIG. 4 is a cross-sectional view showing the lead along line 4-4 in FIG. 3.

FIG. 4 is a cross-sectional view showing the lead 14 along line 4-4 in FIG. 3. As further shown in FIG. 4, and in some embodiments, the outer conductor wire 44 is formed from a small diameter wire to decrease the effective pitch of the wire 44, which, in turn, increases the inductance of the wire 44. In some embodiments, for example, the wire diameter $D_1$ of the outer conductor wire 44 is in the range of between about 0.001 to 0.006 inches, and more specifically, about 0.003 to 0.004 inches. The wire diameter $D_1$ of the outer conductor wire 44 may be greater or lesser, however, depending on the type of lead employed, the configuration of the lead, as well as other factors. Due to the relatively small diameter $D_1$ of the outer conductor wire 44, a greater number of coil turns is present along the length of the lead 14 in comparison to more conventional leads with larger wire diameters, which increases the impedance of the conductor wire 44. This increased impedance aids in reducing the energy dissipated into the surrounding body tissue at or near the lead electrode(s) 30.

The overall diameter $D_2$ of the outer conductor wire 44 can also be increased to further increase the inductance of the wire 44. In some embodiments, for example, the overall diameter $D_2$ of the outer conductor wire 44 is in the range of between about 0.051 to 0.068 inches, and more specifically, about 0.053 to 0.066 inches. The overall diameter of the outer conductor wire 44 may be greater or lesser, however, depending on the type of lead employed, the configuration of the lead, as well as other factors. In some embodiments, the overall diameter of the lead 14 is in the range of between about 3 to 7 Fr, and more specifically, between about 5 to 6 Fr.

In some embodiments, the outer conductor wire 44 is formed from a drawn-filled tube having an outer tubular layer of low-resistive metal or metal-alloy such as MP35N filled with an inner core of electrically conductive material such as silver. Once filled and drawn, the tube is then coiled into a helical shape and attached to the lead 14 using conventional techniques know in the art. In one embodiment, the outer conductor wire 44 comprises a silver-filled MP35N wire having a silver content of about 28% by cross-sectional area. In use, the relatively low resistance of the outer tubular metal or metal-alloy forming part of the outer conductor wire 44 can be used to offset the increased resistance imparted to the wire 44 from using a smaller diameter wire, as discussed above. In some embodiments, the material or materials forming the outer conductor wire 44 can also be selected so as to impart greater flexibility to the wire 44.

The outer conductor wire 44 may be formed from a material or materials different than the inner conductor wire 42. In one embodiment, for example, the wire filars forming the outer conductor wire 44 may comprise a silver-filled MP35N material having a silver content (by cross-sectional area) of about 28% whereas the wire filars forming the inner conductor wire 42 may have a silver content (by cross-sectional area) lower than 28%.

As further shown in FIG. 4, and in some embodiments, the inner conductor wire 42 has a wire diameter $D_3$ of between about 0.001 to 0.004 inches, and more specifically, about 0.002 inches. In certain embodiments, the outer diameter $D_4$ of the inner conductor wire 42 is between about 0.020 to 0.028 inches, and more specifically, between about 0.022 to 0.023 inches. The dimensions of the inner conductor wire 42, including the wire diameter $D_3$ and outer diameter $D_4$ may vary, however.

By increasing the inductance of the lead 14, and in particular the inductance of the outer conductor wire 44, the lead 14 is configured to dissipate RF electromagnetic energy received during a magnetic resonance imaging procedure. This dissipation of electromagnetic energy results in a reduction in heating of body tissue at the location of the electrode(s) 30. The increase in inductance of the lead 14 also reduces the effects of the electromagnetic energy on the therapeutic electrical current delivered through the lead 14, and in some cases, may permit the lead 14 to continue to provide therapy during the MRI procedure. In some embodiments, for example, the increase in inductance of the lead 14 allows the lead 14 to function at normal device frequencies (e.g., 0.5 Hz to 500 Hz) while acting as a poor antenna at MRI frequencies.

While the illustrative lead 14 is described with respect to a cardiac lead for use in providing pacing to a patient's heart 16, the construction of the lead 14 may also be applicable to other medical devices that operate in the presence of electromagnetic fields. For example, the construction of the lead 14, including the inner and outer conductor wires 42, 44, may be used in neural leads adapted for use in neurological applications that utilize MRI imaging.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A medical device, comprising:
   a pulse generator;
   a lead electrically coupled to the pulse generator, the lead including an inner electrode conductor wire helically disposed along all or a portion of a length of the lead, the inner electrode conductor wire having a hollowed, multifilar configuration including six or more co-radially wound wire filars, each filar of the inner electrode conductor wire comprising a first material having a resistance;
   an outer electrode conductor wire helically disposed about and spaced apart from the inner electrode conductor wire along all or a portion of the length of the lead, the outer electrode conductor wire having a single or double filar configuration, each filar of the outer electrode conductor wire comprising a second material having a resistance less than the resistance of the first material;
   at least one insulation layer disposed radially about the inner electrode conductor wire; and
   wherein the outer electrode conductor wire is configured to dissipate electromagnetic energy received by the lead during a magnetic resonance imaging procedure.

2. The medical device of claim 1, wherein the inner electrode conductor wire includes twelve co-radially wound wire filars.

3. The medical device of claim 1, wherein each wire filar of the inner electrode conductor wire has a wire diameter of between about 0.001 to 0.004 inches.

4. The medical device of claim 1, wherein the inner electrode conductor wire has an outer diameter of between about 0.020 to 0.028 inches.

5. The medical device of claim 1, wherein the first material comprises a silver-filled MP35N material having a silver content of less than about 28% by cross-sectional area.

6. The medical device of claim 5, wherein the second material comprises a silver-filled MP35N material having a silver content of about 28% by cross-sectional area.

7. The medical device of claim 1, wherein the outer electrode conductor wire comprises a single filar wire.

8. The medical device of claim 1, wherein the outer electrode conductor wire comprises a double filar wire.

9. The medical device of claim 1, wherein the outer electrode conductor wire has a wire diameter of between about 0.001 to 0.006 inches.

10. The medical device of claim 1, wherein the outer electrode conductor wire has an outer diameter of between about 0.051 to 0.068 inches.

11. The medical device of claim 1, wherein the at least one insulation layer comprises:
    a first insulation layer disposed about the outer electrode conductor wire; and
    a second insulation layer interposed between the outer electrode conductor wire and the inner electrode conductor wire.

12. An implantable medical lead, comprising:
    an inner electrode conductor wire helically disposed along all or a portion of a length of the lead, the inner electrode conductor wire having a hollowed, multifilar configuration including six or more co-radially wound wire filars, each of the wire filars of the inner electrode conductor wire formed of a silver-filled MP35N material;
    an outer electrode conductor wire helically disposed about and spaced apart from the inner electrode conductor wire along all or a portion of the length of the lead, the outer electrode conductor wire having a single or double filar configuration, each of the wire filars of the outer electrode conductor wire formed of a silver-filled MP35N material having a different silver content than the inner electrode conductor wire;
    at least one insulation layer disposed radially about the inner electrode conductor wire; and
    wherein the outer electrode conductor wire is configured to dissipate electromagnetic energy received by the lead during a magnetic resonance imaging procedure.

13. The medical lead of claim 12, wherein the inner electrode conductor wire includes twelve co-radially wound wire filars.

14. The medical lead of claim 12, wherein each wire filar of the inner electrode conductor wire has a wire diameter of between about 0.001 to 0.004 inches.

15. The medical lead of claim 12, wherein the inner electrode conductor wire has an outer diameter of between about 0.020 to 0.028 inches.

16. The medical lead of claim 12, wherein each wire filar of the inner electrode conductor wire comprises a silver-filled MP35N material having a silver content of less than about 28% by cross-sectional area.

17. The medical lead of claim 16, wherein each wire filar of the outer electrode conductor wire comprises a silver-filled MP35N material having a silver content of about 28% by cross-sectional area.

18. The medical lead of claim 12, wherein the outer electrode conductor wire has a wire diameter of between about 0.001 to 0.006 inches.

19. The medical lead of claim 12, wherein the outer electrode conductor wire has an overall diameter of between about 0.051 to 0.068 inches.

20. An implantable medical lead, comprising:
    an inner electrode conductor wire helically disposed along all or a portion of a length of the lead, the inner electrode conductor wire having a hollowed, multifilar configuration including six or more co-radially wound wire filars, each filar of the inner electrode conductor wire comprising a first material having a resistance;
    an outer electrode conductor wire helically disposed about and spaced apart from the inner electrode conductor wire along all or a portion of the length of the lead, the outer electrode conductor wire having a single or double filar configuration, each filar of the outer electrode conductor wire comprising a second material having a resistance less than the resistance of the first material, each of the wire filars of the outer electrode conductor wire having a wire diameter of between about 0.001 to 0.006 inches;
    at least one insulation layer disposed radially about the inner electrode conductor wire; and
    wherein the outer electrode conductor wire is configured to dissipate electromagnetic energy received by the lead during a magnetic resonance imaging procedure.

* * * * *